US006576724B2

(12) United States Patent
Olivier-Bourbigou et al.

(10) Patent No.: US 6,576,724 B2
(45) Date of Patent: Jun. 10, 2003

(54) CATALYTIC COMPOSITION AND PROCESS FOR THE CATALYSIS OF DIMERIZATION CODIMERIZATION AND OLIGOMERIZATION OF OLEFINS

(75) Inventors: Helene Olivier-Bourbigou, Rueil Malmaison (FR); Dominique Commereuc, Meudon (FR); Stephane Harry, Montesson (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/815,347

(22) Filed: Mar. 23, 2001

(65) Prior Publication Data

US 2001/0049398 A1 Dec. 6, 2001

(30) Foreign Application Priority Data

Mar. 23, 2000 (FR) .............................. 00 03819

(51) Int. Cl.⁷ .................................. C08F 4/60
(52) U.S. Cl. .................. 526/139; 526/134; 526/141; 526/157; 526/161; 526/169.1; 526/171; 526/172; 502/121; 502/123; 502/124; 502/164; 502/167
(58) Field of Search ................ 502/103, 164, 502/167; 526/161, 169.1, 171, 172, 154; 556/138

(56) References Cited

U.S. PATENT DOCUMENTS

| 5,166,114 A | | 11/1992 | An-hsiang ............... 502/117 |
| 5,324,799 A | | 6/1994 | Yano et al. .............. 526/139 |
| 5,728,839 A | * | 3/1998 | Herrmann et al. ........ 548/103 |
| 6,060,568 A | * | 5/2000 | Cavell et al. ............ 526/131 |

FOREIGN PATENT DOCUMENTS

| DE | 44 47 066 A1 | 7/1996 | |
| EP | 646412 A1 * | 9/1994 | ............ B01J/31/24 |
| EP | 0 646 412 a1 | 4/1995 | |
| EP | 0 798 041 A1 | 10/1997 | |
| FR | 2 728 180 | 6/1996 | |
| WO | WO 98/27064 A1 * | 6/1998 | ......... C07D/233/68 |

* cited by examiner

Primary Examiner—David W. Wu
Assistant Examiner—Rip A Lee
(74) Attorney, Agent, or Firm—Millen, White, Zelano & Branigan, P.C.

(57) ABSTRACT

A catalytic composition for the dimerization, the codimerization or the oligomerization of olefins results from the dissolution of at least one nickel complex that contains a heterocyclic carbene in a liquid mixture that comprises at least one ammonium halide or quaternary phosphonium halide, at least one aluminum halide and optionally at least one organometallic aluminum compound. It is used in a process of dimerization, codimerization or oligomerization of olefins.

25 Claims, No Drawings

CATALYTIC COMPOSITION AND PROCESS FOR THE CATALYSIS OF DIMERIZATION CODIMERIZATION AND OLIGOMERIZATION OF OLEFINS

CROSS-REFERENCE TO RELATED APPLICATION

This application is related to our concurrently filed application entitled "Catalytic Composition And Process For The Catalysis Of Dimerization, Codimerization And Oligomerization Of Olefins", application Ser. No. 09/815,332 filed Mar. 23, 2001, based on French Priority Application No. 00/03.819, filed Mar. 23, 2000.

FIELD OF THE INVENTION

This invention relates to the catalytic dimerization, codimerization and oligomerization of olefins.

It has as its object a new catalytic composition, the codimerization or result of the dissolution of at least one nickel complex that contains at least one heterocyclic carbene ligand, in the liquid mixture, of ionic type, at least one ammonium halide and/or quaternary phosphonium halide, at least one aluminum trihalide and optionally at least one alkylaluminum halide. This invention also has as its object the use of this catalytic composition in processes of dimerization, codimerization and/or oligomerization of olefins.

BACKGROUND OF THE INVENTION

Some organometallic nickel complexes that contain heterocyclic carbene ligands have been described in the prior art (International Application WO-A-99/6004, U.S. Pat. No. 5,728,839 and Patent Application EP-A-0 798 041). Application WO-A-99/6004 also describes the use of these complexes for the polymerization of acrylates and the hydrocyanation of olefins. Such complexes have the advantage of being very stable. More particularly, these monocarbene or bicarbene ligands lead to nickel complexes that are thermally and chemically stable primarily with regard to oxidation.

Some of these nickel complexes, however, exhibit the drawback of being very non-soluble in standard organic solvents, which limits use thereof. International Patent Application WO-A-99/6004 describes the preparation of carbenic cationic nickel complexes that are water-soluble. The use of water, however, cannot become general in reactions whose active catalytic radical involves a metal-carbon bond, which deteriorates in quality in the presence of protons. This is the case of the dimerization or oligomerization of the olefins.

French Patent FR-B-2 611 700 describes the use of ionic liquids that are formed by aluminum halides and quaternary ammonium halides as solvents of organometallic nickel complexes for the catalysis of dimerization of olefins. The use of such immiscible media with the aliphatic hydrocarbons, in particular with the products that are obtained from the dimerization of olefins, makes possible a better use of homogeneous catalysts. French Patent FR-B-2 659 871 describes a liquid ionic composition that results from bringing into contact at least one quaternary ammonium halide and/or quaternary phosphonium halide with at least one alkylaluminum dihalide and optionally in addition at least one aluminum trihalide. This patent also describes the use of these media as solvents of transition metal complexes, in particular nickel complexes that do not contain a nickel-carbon bond, which are transformed into catalysts for oligomerization of olefins. Below, these media will be called "molten salts" because they are liquid at moderate temperature.

During these works, it was shown that the most active nickel catalysts are obtained in "molten salts" that consist of a molar equivalent of quaternary ammonium halide and/or quaternary phosphonium halide with an equivalent (or more) of aluminum trihalide and optionally any amount of alkylaluminum dihalide. This formulation has proven particularly advantageous because the nickel complexes that are dissolved in it have a high catalytic activity.

The neutral ligands that are described in these works and optionally associated with nickel are tertiary phosphines. The drawback of the alkylphosphine ligands is that these are expensive compounds that oxidize easily in the presence of air.

SUMMARY OF THE INVENTION

It has now been found that the nickel complexes that carry at least one monocarbene or bicarbene ligand that correspond, for example, to formulas (I) and (II) that are provided below are soluble and stable in the "molten salts" media and that they make it possible to catalyze the dimerization, codimerization or oligomerization of olefins. These carbene ligands were the object of a survey in Angew. Chem. Int. Ed. Engl. 1997, 36, 2162. These are σ-donor ligands and π-acceptor ligands that form very stable bonds with the transition metals. Their electronic properties can be compared to those of basic trialkylphosphines.

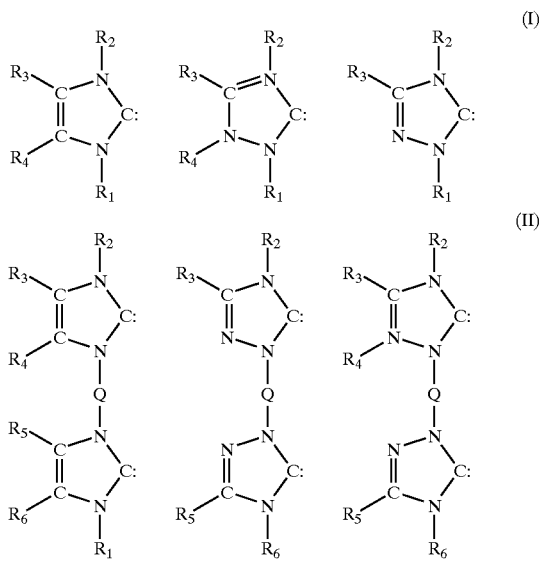

The invention therefore has as its object a catalytic composition that results from the dissolution of a nickel compound that contains at least one heterocyclic mono- or bicarbene ligand in a "molten salt" medium that consists of at least one quaternary ammonium halide and/or at least one quaternary phosphonium halide (Product A), at least one aluminum halide (Product B), and optionally at least one organic aluminum compound (Product C).

DETAILED DESCRIPTION OF THE INVENTION

The nickel compounds that are used according to the invention are salts of nickel or organometallic compounds that may or may not be charged and that correspond to the general formula (already described in Patent Application EP-A-0 798 041):

$(Ni_aX_bY_dL_c)^n(A)_n$ in which:

a, b, c, d and n are integers with a equal to 1, 2 or 3; b equal to 0 to 2 times a; d equal to 0 to 2 times a; c is at least 1; n equal to 0, 1 or 2;

X and Y, identical or different, each represent a mono- or multidentate ligand that may or may not be charged; by way of examples, it is possible to cite halides, carboxylates (for example ethyl-2-hexanoate), acetylacetonate, sulfate, phenates, mono- and di-olefins, π-aromatic compounds, alkyl or aryl radicals, phosphines, phosphites and carbon monoxide;

L is a heterocyclic mono- or bi-carbene that corresponds to, for example, one of general formulas (I) and (II) above, in which $R_1$, $R_2$, $R_3$, $R_4$, $R_5$ and $R_6$, identical or different, each represent hydrogen, a hydrocarbon-containing group, aliphatic group, saturated or unsaturated group, or aromatic group, comprising 1 to 12 carbon atoms, and Q represents an aliphatic bivalent radical with 1 to 4 carbon atoms; and A is a sparingly coordinating anion; by way of examples, it is possible to cite tetrafluoroborate anions, hexafluorophosphate anions, tetraphenylborate anions and derivatives thereof, tetrachloroaluminate anions, hexafluoroantimonate anions, trifluoroacetate anions, trifluoromethylsulfonate anions and acetate anions.

Heterocyclic carbenes L can be generated from corresponding imidazolium or bis(azolium) salts by deprotonation. The transition metal can play the role of reducing agent.

By way of nonlimiting examples of heterocyclic mono- or bicarbene ligands, the carbene ligands that are described by formulas (1), (2) and (3) that are given below will be cited.

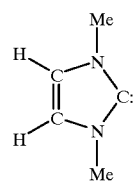

(1)

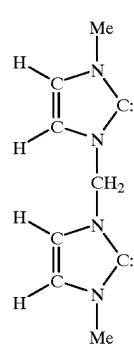

(2)

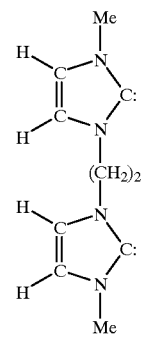

(3)

By way of nonlimiting examples of nickel compounds that can be used according to the invention, it is possible to cite the complexes of $NiCl_2$, [dimethyl-1,3-imidazolylidene-2]$_2$; $NiI_2$, [dimethyl-1,3-imidazolylidene-2]$_2$; π-allyl nickel chloride (dimethyl-1,3-imidazolylidene-2); $NiCl_2$, [dimethyl-1,1'-imidazole-diylidene-2,2'-methylene-3,3']$_2$; $NiCl_2$, [dimethyl-1,1'-imidazole-diylidene-2,2'-ethylene-3,3']$_2$; $NiI_2$ [dimethyl-1,1'-imidazole-diylidene-2,2'-methylene-3,3']$_2$ and $NiI_2$ [dimethyl-1,1'-imidazole-diylidene-2,2'-methylene-3,3']$_2$.

The "molten salts" that are employed according to the invention consist of:

a) at least one halide, more particularly a chloride and/or a bromide, quaternary ammonium and/or quaternary phosphonium (A);

b) at least aluminum trichloride and/or aluminum tribromide (B); and c) optionally an organic aluminum compound (C).

The quaternary ammonium and/or phosphonium halides that can be used within the scope of the invention (Product A) preferably correspond to one of general formulas $NR^1R^2R^3R^4X$ (with the exception of $NH_4X$), $PR^1R^2R^3R^4X$, $R^1R^2N—CR^3R^4X$ or $R^1R^2 P=CR^3R^4X$, in which X represents Cl or Br and $R^1$, $R^2$, $R^3$ and $R^4$, identical or different, each represent hydrogen or a hydrocarbyl radical with 1 to 12 carbon atoms, for example alkyl groups, saturated or unsaturated groups, cycloalkyl or aromatic groups, aryl or aralkyl groups comprising 1 to 12 carbon atoms, whereby it is understood that preferably a single one of substituents $R^1$, $R^2$, $R^3$ and R4 represents hydrogen; or else one of general formulas:

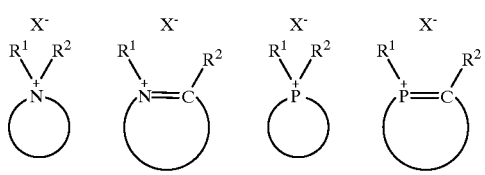

in which the nitrogen-containing heterocycles or phosphorus-containing heterocycles that comprise 1, 2 or 3 nitrogen atoms and/or phosphorus atoms consist of 4 to 10 atoms, and X, $R^1$ and $R^2$ are defined as above.

By way of examples, it is possible to cite tetrabutylphosphonium chloride, N-butylpyridinium chloride, ethylpyridinium bromide, butyl-3 methyl-1 imidazolium chloride, diethylpyrazolium chloride, pyridinium chlorohydrate, trimethylphenylammonium chloride and ethyl-3 methyl-1 imidazolium chloride. These salts can be used alone or in mixtures.

The aluminum halides that are used as Product B in the composition of "molten salts" according to the invention are essentially aluminum chloride and aluminum bromide.

The organic compounds of the aluminum that are used optionally as Products C in the composition of "molten salts" according to the invention have as a general formula $AlR_xX_{3-x}$, in which R is a hydrocarbon-containing radical, for example, alkyl, linear or branched, comprising 2 to 8 carbon atoms, whereby X is chlorine or bromine and x has a value that is equal to 1, 2 or 3.

By way of examples, it is possible to use isobutylaluminum sesquichloride, ethylaluminum sesquichloride, dichloroisobutylaluminum, dichloroethylaluminum or chlorodiethylaluminum.

The components of "molten salts" as defined above are in general used in molar ratios A:B of 1:0.5 to 1:3, preferably 1:1 to 1:2; Product C is used in a molar ratio with Product B that is at most equal to 100:1 and preferably 0.005:1 to 10:1. It is still necessary that the components and their ratios be such that the mixture is liquid at the temperature at which the nickel compound is introduced although the catalytic reaction of dimerization, codimerization or oligomerization can be carried out at a temperature that is less than or greater than the melting point of the catalytic composition.

The compounds that are part of the composition according to the invention can be mixed in any order. The mixture can be made by simply bringing the components into contact, followed by stirring until a homogeneous liquid is formed.

The olefins that can be dimerized, codimerized or oligomerized by the catalytic compositions according to the invention are ethylene, propylene, n-butenes and n-pentenes, alone or in a mixture, pure or diluted by one or more alkane(s), such as are found in "fractions" that are obtained from petroleum refining processes, such as catalytic cracking or steam-cracking.

The catalytic reaction of dimerization, codimerization or oligomerization of olefins can be conducted in a closed system, in a semi-open system or continuously with one or more reaction stages. A vigorous stirring should ensure good contact between the reagent or reagents and the catalytic mixture. The reaction temperature can be −40 to +70° C., preferably −20 to +50° C. It is possible to operate above or below the melting point of the medium, whereby the dispersed solid state does not keep the reaction from proceeding smoothly. The heat that is produced by the reaction can be eliminated by all of the means that are known to one skilled in the art. The pressure can be between the atmospheric pressure and 200 atmospheres (about 20 MPa), preferably between atmospheric pressure and 50 atmospheres (about 5 MPa). The products of the reaction and the reagent or reagents that have not reacted are separated from the catalytic system by simple decanting, then are fractionated.

The following examples illustrate the invention without limiting its scope.

EXAMPLE 1

Preparation of the Ionic Solvent 17.5 g (0.1 mol) of butylmethylimidazolium chloride, 16.3 g (0.122 mol) of sublimed aluminum trichloride, and 1.42 g (0.0112 mol) of dichloroethylaluminum are mixed at ambient temperature. A liquid composition is obtained.

EXAMPLE 2

Preparation of the Nickel Complex $NiI_2$, [dimethyl-1,3-imidazolylidene-2]$_2$:

The nickel complex is prepared by an improvement of the synthesis that is described in Organometallics, 1997, 16, 2209.

In a Schlenk tube, pre-dried nickel acetate (6 mmol) is vigorously stirred with dimethyl-1,3-imidazolium iodide (12 mmol) in nitromethane (60 mL). It is heated to 150° C. by putting the pump under vacuum for an hour. It is allowed to cool, then the red complex that is formed is extracted with hot tetrahydrofuran (500 mL). The tetrahydrofuran is then evaporated under a vacuum, and the red compound is washed with diethyl ether (140 mL). A second washing with absolute ethanol (15 mL) is necessary to eliminate the dimethyl-1,3 imidazolium iodide that has not reacted.

EXAMPLE 3

Dimerization of Butene

A 100 mL glass reactor that is equipped with a probe for measuring temperature, a small magnetized bar to ensure good stirring and a double jacket that allows the circulation of a cooling liquid was purged of air and moisture and kept at the atmospheric pressure of butene-1. 50.2 mg (0.1 mmol) of the complex $NiI_2$, [dimethyl-1,3-imidazolylidene-2]$_2$ obtained in Example 2 was introduced, then the temperature was lowered to 10° C. and 5 ml of the liquid composition obtained in Example 1 was injected with a syringe. Stirring was started, and absorption of butene was observed immediately. When the reactor was three quarters full of liquid, stirring was stopped, the "molten salt" was decanted, and the bulk of the hydrocarbon-containing phase was drawn off. The operation was restarted five times. The total duration of the reaction is 5 hours and 25 minutes. At this time, a total of 240 g of butene was introduced. 24 kg of products per gram of Ni was produced. The analysis of various fractions showed that they consisted of 94–96% by weight of dimers.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications cited above and below, and of corresponding French application 00/03.819, are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A catalytic composition obtained from a process comprising dissolving at least one nickel compound that contains at least one heterocyclic mono- or bicarbene ligand in a medium comprising:

(A) at least one member selected from the group consisting of at least one quaternary ammonium halide and at least one quaternary phosphonium halide;

(B) at least one aluminum halide; and optionally (C) at least one organic aluminum compound.

2. A catalytic composition according to claim 1, wherein said nickel compound corresponds to general formula $(Ni_aX_bY_dL_c)^{n+}(A)_n$, wherein:

a, b, c, d and n are integers with a equal to 1, 2 or 3; b equal to 0 to 2 times a; c is at least 1; and n equal to 0, 1 or 2;

X and Y, identical or different, each represent an optionally charged mono or multidentate ligand;

L is a heterocyclic mono- or bi-carbene ligand; and

A is a coordinating anion.

3. A catalytic composition according to claim 2, wherein (c) is other than zero and wherein ligand L corresponds to one of following formulas (I) and (II):

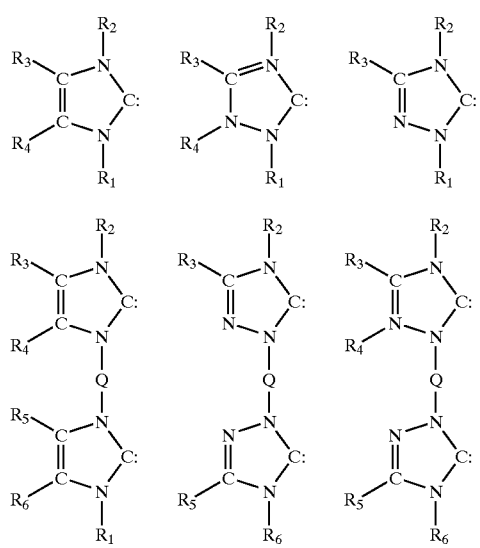

wherein $R_1$, $R_2$, $R_3$, $R_4$, $R_5$ and $R_6$, identical or different, each represent hydrogen, a hydrocarbon-containing group, an aliphatic group, a saturated or unsaturated group, or an aromatic group comprising 1 to 12 carbon atoms, and Q represents an aliphatic bivalent radical with 1 to 4 carbon atoms.

4. A catalytic composition according to claim 2, wherein L corresponds to at least one of formulas (1), (2) and (3):

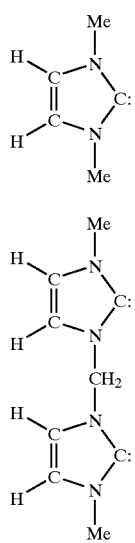

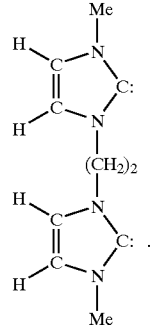

5. A catalytic composition according to claim 2, wherein (b) and/or (d) is other than zero and wherein X and Y represent at least one of a halide, a carboxylate, an acetylacetonate, a sulfate, a phenate, a mono- and di-olefin, a π-aromatic compound, an alkyl or aryl radical, a phosphine, a phosphite or carbon monoxide.

6. A catalytic composition according to claim 2, wherein A comprises at least one anion selected from the group consisting of tetrafluoroborate, hexafluorophosphate, a tetraphenylborate, tetrachloroaluminate, hexafluoroantimonate, trifluoroacetate, trifluoromethylsulfonate and acetate.

7. A catalytic composition according to claim 2, wherein the aluminum halide is aluminum trichloride or aluminum tribromide.

8. A catalytic composition according to claim 2, wherein (A) and (B) are used in a molar ratio (A):(B) of 1:0.5 to 1:3.

9. A catalytic composition according to claim 2, wherein at least one ligand L is of the formula:

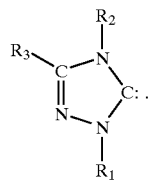

10. A catalytic composition according to claim 2, wherein at least one ligand L is of the formula:

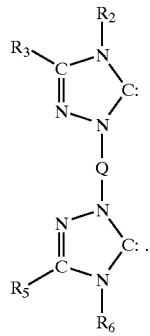

11. A catalytic composition according to claim 1, wherein the nickel compound is:

NiCl$_2$, [dimethyl-1,3-imidazolylidene-2]$_2$;
NiI$_2$, [dimethyl-1,3-imidazolylidene-2]$_2$;
π-allyl nickel chloride (dimethyl-1,3-imidazolylidene-2);

NiCl$_2$ [dimethyl-1,1'-imidazole-diylidene-2,2'-methylene-3,3']$_2$;

NiCl$_2$ [dimethyl-1,1'-imidazole-diylidene-2,2'-ethylene-3,3']$_2$;

NiI$_2$ [dimethyl-1,1'-imidazole-diylidene-2,2'-methylene-3,3']$_2$; or

NiI$_2$ [dimethyl-1,1'-imidazole-diylidene-2,2'-ethylene-3,3']$_2$.

12. A catalytic composition according to claim 11, wherein the quaternary ammonium halide or quaternary phosphonium halide is tetrabutylphosphonium chloride, N-butylpyridinium chloride, ethylpyridinium bromide, 1-methyl-3-butyl-imidazolium chloride, N,N-diethylpyrazolium chloride, pyridinium chlorohydrate, trimethylphenylammonium chloride or 1-ethyl-3-methyl-imidazolium chloride.

13. A catalytic composition according to claim 12, wherein the aluminum halide is aluminum trichloride or aluminum tribromide.

14. A catalytic composition according to claim 1, wherein the quaternary ammonium halide or quaternary phosphonium halide corresponds to:

one of general formulas:

NR$^1$R$^2$R$^3$R$^4$X, with the exception of NH$_4$X, PR$^1$R$^2$R$^3$R$^4$X, R$^1$R$^2$N=CR$^3$R$^4$X or R$^1$R$^2$P=CR$^3$R$^4$X, in which X represents Cl or Br, and R$^1$, R$^2$, R$^3$ and R$^4$, identical or different, each represent hydrogen or a hydrocarbyl radical with 1 to 12 carbon atoms;

or one of general formulas:

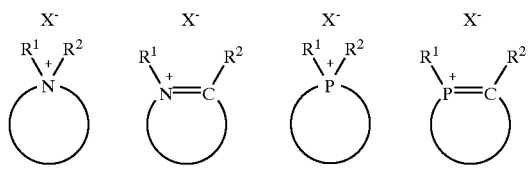

in which the nitrogen-containing heterocycles or phosphorus-containing heterocycles comprise 1, 2 or 3 heteroatoms selected from the group consisting of nitrogen atoms and phosphorus atoms and have 4 to 10 ring atoms, and X, R$^1$ and R$^2$ are defined as above.

15. A catalytic composition according to claim 14, wherein the quaternary ammonium halide or quaternary phosphonium halide is tetrabutylphosphonium chloride, N-butylpyridinium chloride, ethylpyridinium bromide, 1-methyl-3-butyl-imidazolium chloride, N,N-diethylpyrazolium chloride pyridinium chlorohydrate, trimethylphenylammonium chloride or 1-ethyl-3-methyl-imidazolium chloride.

16. A catalytic composition according to claim 1, wherein the medium also comprises (C).

17. A catalytic composition according to claim 16, wherein (C) corresponds to general formula AlR$_x$X$_{3-x}$, in which R is an alkyl, linear or branched radical, comprising 2 to 8 carbon atoms, X is chlorine or bromine and X has a value that is equal to 1, 2 or 3.

18. A catalytic composition according to claim 16, wherein (C) is isobutylaluminum sesquichloride, ethylaluminum sesquichloride, dichloroisobutylaluminum, dichloroethylaluminum or chlorodiethylaluminum.

19. A catalytic composition according to claim 16, comprising (C) in a molar ratio to (B) of at most equal to 100:1.

20. A process of dimerization, codimerization or oligomerization of at least one olefin, comprising contacting said at least one olefin with a catalytic composition according to claim 1.

21. A process according to claim 20, wherein the reaction of dimerization, codimerization or oligomerization of the olefins is conducted in a closed system, semi-open system or continuously with one or more reaction stages, while being stirred and at a temperature of −40 to +70° C.

22. A process according to claim 21, wherein the olefin(s) is (are) selected from the group consisting of ethylene, propylene, n-butenes and n-pentenes, and mixtures thereof, optionally diluted by at least one alkane.

23. A process according to claim 20, wherein the olefins(s) is (are) contained in a fraction that is obtained from a petroleum refining process.

24. A catalytic composition according to claim 1, essentially free of aromatic solvents.

25. A catalytic composition according to claim 1, wherein the at least one heterocyclic ligand is devoid of endocyclic phosphorus.

* * * * *

UNITED STATES PATENT AND TRADEMARK OFFICE
CERTIFICATE OF CORRECTION

PATENT NO. : 6,576,724 B2  
DATED : June 10, 2003  
INVENTOR(S) : Helene Olivier-Bourbigou et al.

It is certified that error appears in the above-identified patent and that said Letters Patent is hereby corrected as shown below:

Title page, Item [54], Column 1, line 2,
Title, reads "DIMERIZATION" should read -- DIMERIZATION, --

Column 7,
Line 2, reads "c is at least 1;" should read -- d equal to 0 to 2 times a;
c is at least 1; --
Line 11, reads "of following," should read  -- of the following --

Column 10,
Line 6, reads "chloride pyridinium" should read -- chloride, pyridinium --

Signed and Sealed this

Twentieth Day of July, 2004

JON W. DUDAS
*Acting Director of the United States Patent and Trademark Office*